US011730898B2

(12) United States Patent
Purkins et al.

(10) Patent No.: US 11,730,898 B2
(45) Date of Patent: Aug. 22, 2023

(54) INHALER

(71) Applicant: MERXIN LTD, King's Lynn (GB)

(72) Inventors: Graham Purkins, King's Lynn (GB); Carol Balfour, Norwich (GB); Gavin Kovacs, Norwich (GB); Philippe Rogueda, Pessac (FR)

(73) Assignee: MERXIN LTD, King's Lynn (GB)

( * ) Notice: Subject to any disclaimer, the term of this patent is extended or adjusted under 35 U.S.C. 154(b) by 668 days.

(21) Appl. No.: 16/757,708

(22) PCT Filed: Oct. 5, 2018

(86) PCT No.: PCT/GB2018/052846
§ 371 (c)(1),
(2) Date: Apr. 20, 2020

(87) PCT Pub. No.: WO2019/081883
PCT Pub. Date: May 2, 2019

(65) Prior Publication Data

US 2020/0384218 A1 Dec. 10, 2020

(30) Foreign Application Priority Data

Oct. 24, 2017 (GB) ..................................... 1717451

(51) Int. Cl.
*A61M 15/00* (2006.01)

(52) U.S. Cl.
CPC ...... *A61M 15/0041* (2014.02); *A61M 15/003* (2014.02); *A61M 15/0026* (2014.02); *A61M 15/0028* (2013.01); *A61M 15/0035* (2014.02)

(58) Field of Classification Search
CPC .......... A61M 15/0041; A61M 15/0026; A61M 15/0033–0035; A61M 11/002; A61M 15/0028; A61M 15/003
See application file for complete search history.

(56) References Cited

U.S. PATENT DOCUMENTS 5,947,118 A * 9/1999 Hochrainer ....... A61M 15/0035 128/203.15
8,746,244 B2 6/2014 Kaemper et al.
(Continued)

FOREIGN PATENT DOCUMENTS

CN 103237570 A 8/2013
CN 106456911 A 2/2017
(Continued)

OTHER PUBLICATIONS

English translation for CN 107041986, translated by Search Clarivate Analytics, translated on May 3, 2023.*
(Continued)

*Primary Examiner* — Tu A Vo
(74) *Attorney, Agent, or Firm* — ArentFox Schiff LLP

(57) ABSTRACT

An inhaler for inhalation of an inhalable dry powder is provided. The inhaler has (a) an outer shell having a first shell part and a second shell part; (b) a capsule holder having a chamber for holding a capsule, a capsule breaker for breaking open a capsule held within the chamber and a trigger for causing the capsule breaker to break open a capsule; (c) a support for supporting the capsule holder; and (d) an outlet for passage of dry powder from the capsule into a user. The capsule holder is positioned in the first shell part which has an aperture through which the trigger protrudes. The aperture has a cut-out in the rim of the first shell part and through which the trigger may pass when the capsule holder is removed from the first shell part. The support has one or more first mating parts for mating with one or more second mating parts on the first shell part, the first and second mating parts preventing outward movement of the walls of the first shell part when the first and second mating parts are mutually engaged.

13 Claims, 9 Drawing Sheets

(56) References Cited

U.S. PATENT DOCUMENTS

| | | | | |
|---|---|---|---|---|
| 10,556,069 | B2 * | 2/2020 | Bhide | A61M 15/0026 |
| 10,998,093 | B2 * | 5/2021 | Sutherland | A61M 15/0091 |
| 2003/0235538 | A1 * | 12/2003 | Zierenberg | A61M 15/0026 128/200.23 |
| 2004/0149283 | A1 * | 8/2004 | Hochrainer | A61M 15/0005 128/203.15 |
| 2006/0237016 | A1 * | 10/2006 | Wachtel | A61M 15/0028 128/205.21 |
| 2008/0295832 | A1 * | 12/2008 | Geser | A61M 15/0035 128/207.14 |
| 2013/0255679 | A1 * | 10/2013 | Andrade | A61M 15/003 128/203.15 |
| 2014/0318538 | A1 * | 10/2014 | Bilgic | A61M 15/0028 128/203.15 |
| 2016/0022931 | A1 * | 1/2016 | Althorpe | A61M 11/003 128/203.12 |
| 2018/0043111 | A1 * | 2/2018 | Ahern | A61M 15/003 |
| 2018/0344956 | A1 * | 12/2018 | Huang | A61K 31/46 |
| 2019/0076607 | A1 * | 3/2019 | Zeng | A61M 15/0041 |
| 2019/0269866 | A1 * | 9/2019 | Von Schuckmann | A61M 15/0041 |

FOREIGN PATENT DOCUMENTS

| | | | | |
|---|---|---|---|---|
| CN | 106924845 A | * | 7/2017 | |
| CN | 106924845 A | | 7/2017 | |
| CN | 107041986 A | * | 8/2017 | A61M 15/00 |
| CN | 107041986 A | | 8/2017 | |
| EP | 3138601 A1 | | 3/2017 | |
| WO | 9428958 A1 | | 12/1994 | |
| WO | 2012076479 A1 | | 6/2012 | |
| WO | 2014135224 A1 | | 9/2014 | |
| WO | 2015166239 A1 | | 11/2015 | |

OTHER PUBLICATIONS

English translation for CN 106924845, translated by Search Clarivate Analytics, translated on May 3, 2023.*

International Search Report and Written Opinion in PCT/GB2018/052846 dated Dec. 17, 2018.

International Preliminary Report on Patentability in PCT/GB2018/052846 dated Feb. 4, 2020.

Written Opinion in PCT/GB2018/052846 dated Oct. 4, 2019.

* cited by examiner

INHALER

CROSS-REFERENCE TO RELATED APPLICATIONS

This application is a National Stage Entry of PCT/GB2018/052846, filed Oct. 5, 2018, which claims foreign priority to GB Patent Application No. 1717451.7 filed on Oct. 24, 2017, the disclosure of which is hereby incorporated by reference in its entirety.

The present invention relates to inhalers, in particular to inhalers for the inhalation of dry powders from capsules.

Various inhalers exist for the inhalation by a user of a dry powder contained within a capsule. Generally, such inhalers comprise a capsule holder, a mechanism for breaking open a capsule held within the capsule holder and a mouthpiece or nosepiece through which the powder from the capsule can be inhaled. It is known to provide the capsule holder and mouthpiece/nosepiece within a protective hinged outer shell with upper and lower halves of the outer shell connected via a hinge pin or other mechanical coupling. A hinged plate, also pivotable about the hinge pin, separates the upper half of the outer shell from the lower half of the outer shell, and acts as a support for the capsule holder, positioning the capsule holder in the lower half of the hinged outer shell. Conveniently, the hinged plate is attached to the lower half of the outer shell via a "snap-fit" connection so that it can be removed when required but will stay in place during normal use. It is also usual for the capsule holder to include a trigger for actuating the capsule breaking mechanism. Typically, the trigger is in the form of a button which protrudes through an aperture in the lower half of the outer shell. When the button is pressed, a capsule held within a chamber of the capsule holder is pierced by one or more pointed rods and the powder is released. The powder can then be inhaled through the mouthpiece/nosepiece.

WO94/28958 describes such an inhaler in which the button sits within a "cut-out" formed in the rim of the lower half of the shell. This is particularly convenient because it allows the capsule holder and button to be removed from the lower half of the shell when the hinged plate is disconnected and pivoted away from the lower half of the shell. However, the provision of the cut-out makes the lower half of the shell flexible and thus the provision of a reliable "snap-fit" problematic.

In order to solve this problem, EP2648787 describes an inhaler in which the rim of the lower half of the outer shell is complete, with an aperture for the push button provided below the complete outer rim. EP2648787 describes an "assembly" comprising the capsule holder, capsule opening device and button. In order to provide additional structural support to the outer shell, the shape of the assembly is tapered to match the shape of the lower part of the shell.

However, whilst the inhaler described in EP2648787 does provide a rigid lower part of the outer shell, the provision of the complete rim means that it is difficult to remove the capsule holder unless the button is pressed in or removed. Accordingly, the inhaler described in EP264878 is not user friendly. Furthermore, the part of the rim above the aperture is very thin and thus can easily be broken during repeated use.

It is, therefore, an object of the present invention to seek to alleviate the above identified problems.

SUMMARY OF THE INVENTION

According to one aspect of the present invention, there is provided an inhaler for inhalation of an inhalable dry powder, the inhaler comprising:—

(a) an outer shell comprising a first shell part and a second shell part;
(b) a capsule holder comprising a chamber for holding a capsule, a capsule breaker for breaking open a capsule held within the chamber and a trigger for causing the capsule breaker to break open a capsule;
(c) a support for supporting the capsule holder; and
(d) an outlet for passage of dry powder from the capsule into a user,
 - wherein the capsule holder is positioned in the first shell part,
 - wherein the first shell part comprises an aperture through which the trigger protrudes,
 - wherein the aperture comprises a cut-out in the rim of the first shell part and through which the trigger may pass when the capsule holder is removed from the first shell part, and
 - wherein the support comprises one or more first mating parts for mating with one or more second mating parts on the first shell part, said first and second mating parts preventing outward movement of the walls of the first shell part when said first and second mating parts are mutually engaged.

Remarkably, the present invention stabilises the walls of the first shell part such that the integrity of a connection, preferably a snap-fit connection, between the support and the first shell part is maintained. This is despite the presence of a cut-out in the rim of the first shell part.

Preferably, outward movement of opposing walls of the first shell part is prevented.

Preferably, the first shell part comprises the base of the inhaler.

Preferably, the first shell part is a lower shell part and the second shell part is an upper shell part.

Remarkably, the present invention not only allows the provision of a cut-out in the upper rim of the first shell part but, at the same time, overcomes the problem of shell instability caused by a flexible outer wall. Accordingly, the present invention provides an inhaler in which secure, detachable attachment of a hinged plate to the first shell part is achieved with a predetermined and predictable "snap-fit" force, such that the hinged plate stays connected to the lower shell part during use, but can still be removed when desired without accidental detachment by a user.

Preferably, the one or more first mating parts comprise one or more male mating parts, for example one or more protrusions and the one or more second mating parts comprising one or more female mating parts, for example one or more recesses.

Alternatively, the one or more first mating parts comprise one or more female mating parts, for example one or more recesses and the one or more second mating parts comprise one or more male mating parts, for example one or more protrusions.

Preferably, the support comprises a support plate.

Preferably, the support is hinged to the first shell part.

Preferably, the first shell part and the second shell part are connected via a hinge.

Preferably, the support, first shell part and second shell part are connected via a common hinge, preferably a hinge pin.

Preferably, the support comprises one or more third mating parts for mating with one or more fourth mating parts on the first shell part.

Preferably, the one or more third mating parts comprise one or more male mating parts, for example one or more protrusions and the one or more fourth mating parts comprise one or more female mating parts, for example one or more recesses.

Alternatively, the one or more third mating parts comprise one or more female mating parts, for example one or more recesses and the one or more fourth mating parts comprise one or more male mating parts, for example one or more protrusions.

Preferably, engagement of the one or more third mating parts with the one or more fourth mating parts forms a connection, preferably a snap-fit connection, between the support and the first shell part.

Preferably, the connection formed between the support and the first shell part is maintained by engagement of the one or more first mating parts with the one or more second mating parts.

Preferably, the first shell part is a lower shell part and the vertical distance between second and fourth mating parts is less than the length or depth of the first mating parts.

Preferably, the first shell part is a lower shell part and the vertical distance between the one or more second mating parts, preferably the opening of the one or more second mating parts, and an edge, preferably an upper or lower edge, of the one or more fourth mating parts is less than the length or depth of the one or more first mating parts.

Preferably, the length or depth of the one or more first mating parts is between about 2 mm and about 5 mm, preferably between about 2 mm and about 4 mm, preferably about 3 mm.

Preferably, the vertical distance between the one or more second mating parts, preferably the opening of the one or more second mating parts, and an upper or lower edge of the one or more fourth mating parts is between about 0.5 mm and about 2 mm, preferably between about 0.5 mm and about 1.5 mm, preferably about 1 mm.

Preferably, the difference between (a) the distance between the one or more second mating parts and an upper or lower edge of the one or more fourth mating parts, and (b) the length or depth of the one or more first mating parts is between about 1 mm and about 4 mm, preferably between about 1 mm and about 3 mm, preferably about 2 mm.

This means that the third and fourth mating parts disengage from each other before the first and second mating parts when the support is moved out of engagement with the first shell part. This also means that when the support is moved into engagement with the first shell part, the first and second mating parts engage before the third and fourth mating parts. This allows engagement of the first and second mating parts to stabilise the first shell part and allow reliable engagement of the third and fourth mating parts.

This provides rigidity to the first shell part both during and after engagement of a "snap-fit" connection, ensuring that the integrity of the connection is maintained at all times when the support and the first shell part are engaged.

Preferably, the one or more first mating parts extend in a direction substantially perpendicular to the plane of the support.

Preferably, the one or more third mating parts extend in a direction substantially parallel to the plane of the support.

Preferably, the first shell part comprises one or more female mating parts within or on a wall of the first shell part for receiving one or more male mating parts on the support.

Preferably, the first shell part comprises one or more cavities and/or one or more recesses within or on a wall of the first shell part for receiving one or more protrusions on the support.

Preferably, the one or more cavities comprise one or more pockets.

As such, it is preferred that the support comprises one or more protrusions for insertion into one or more cavities within or on a wall of the first shell part.

Preferably, the first shell part comprises one or more recesses within or on a wall of the first shell part for receiving one or more protrusions on the support.

As such, it is preferred that the support comprises one or more protrusions for insertion into one or more recesses within or on a wall of the first shell part.

Preferably, the first shell part comprises one or more cavities for receiving one or more first protrusions on the support, and one or more recesses for receiving one or more second protrusions on the support.

Preferably, the one or more first protrusions project in a direction substantially perpendicular to the plane of the support. Preferably, the first shell part is a lower shell part and the one or more first protrusions project in a downward direction.

Preferably, the one or more first protrusions are downwardly projecting protrusions.

Preferably, the one or more first protrusions are sized such that they engage with the one or more cavities before the one or more second protrusions engage with the one or more recesses when the support is moved into engagement with the first shell part.

Preferably, the one or more second protrusions project in a direction substantially parallel to the plane of the support. Preferably, the first shell part is a lower shell part and the one or more second protrusions project in a lateral/sideways direction. Preferably, the one or more second protrusions are lateral/sideways projecting protrusions.

Preferably, the one or more second protrusions are sized such that they disengage from the one or more recesses before the one or more first protrusions disengage from the one or more cavities when the support is moved out of engagement with the first shell part.

This provides rigidity to the first shell part both during and after engagement of a "snap-fit" connection, ensuring that the integrity of the connection is maintained at all times when the support and the first shell part are engaged.

Preferably, the first shell part is a lower shell part and the vertical distance between (i) the opening of the one or more cavities in the first shell part, and (ii) the upper edge of the opening of the one or more recesses in the first shell part, is less than the length of the one or more first protrusions on the support.

In preferred embodiments:—

(a) the length of the one or more first protrusions is between about 2 mm and about 5 mm, preferably between about 2 mm and about 4 mm, preferably about 3 mm; and (b) the vertical distance between (i) the opening of the one or more cavities, and (ii) the upper edge of the opening of the one or more recesses is between about 0.5 mm and about 2 mm, preferably between about 0.5 mm and about 1.5 mm, preferably about 1 mm.

Preferably, the difference between:—

(a) the distance between (i) the opening of the one or more cavities, and (ii) the upper edge of the opening of the one or more recesses, and (b) the length of the one or more first protrusions, is between about 1 mm and about 4 mm, preferably between about 1 mm and about 3 mm, preferably about 2 mm.

Preferably, when the support is in engagement with the lower shell part, the one or more recesses are adjacent the support and the one or more cavities are below the support.

Preferably, when the support is in engagement with the lower shell part, the one or more recesses are in the same plane as the support and the one or more cavities are below the plane of the support.

Preferably, the one or more second mating parts are formed in or on a support facing surface of the first shell part.

Preferably, the one or more second mating parts are formed in or on a thickened part of the outer wall of the first shell part.

Preferably, the one or more female mating parts, preferably cavities, are formed in a thickened part of the outer wall of the first shell part.

Preferably, the thickened part of the outer wall at least partially surrounds the cut-out and/or the aperture.

Preferably, the thickened part of the outer wall is provided at or near each side of the cut out.

Preferably, the thickened part of the outer wall is provided along at least a part of each side of the aperture adjacent the cut-out. Put another way, it is preferred that the thickened part of the outer wall is provided each side of an upper part of the aperture.

Preferably, at least a part of the thickened part of the outer wall of the first shell part is a double-skinned wall comprising an inner skin and outer skin, with said one or more cavities formed between said inner and outer skins.

Preferably, the double-skinned wall comprises one or more cross members for dividing the space between said inner and outer skins into multiple cavities.

Preferably, the thickness of the thickened part of the wall, preferably the double-skinned wall, tapers from a greater thickness at a point away from the cut-out to a lesser thickness at or near the cut-out.

Preferably, the length of the thickened part of the wall, preferably the double-skinned wall, tapers from a greater length at or near the rim of the first shell part to a lesser length at a point away from the rim of the first shell part, for example at or near the base of the first shell part.

Preferably, the one or more first mating parts are formed in or on a first shell part facing surface of the support.

Preferably, the one or more first mating parts are formed in or on a lower surface of the support.

Preferably, the one or more fourth mating parts are formed in or on an upstanding wall of the first shell part.

Preferably, the one or more third mating parts are formed in or on the edge of the support.

Preferably, the one or more third mating parts are lateral mating parts.

Preferably, the one or more male mating parts, preferably protrusions, protrude from a first shell part facing surface of the support.

Preferably, the one or more male mating parts, preferably protrusions, are positioned at or near the edge of the support.

Whilst a preferred embodiment of the present invention provides male mating parts on the support and female mating parts on the first shell part, it will be appreciated that the first and/or third mating parts could be female mating parts, for example recesses or cavities formed in the support and that the second and/or fourth mating parts could be male mating parts, for example protrusions formed on the first shell part.

Preferably, the first shell part comprises one or more male mating parts within or on a wall of the first shell part for engagement with one or more female mating parts on the support.

Preferably, the support comprises one or more cavities and/or recesses within or on a wall or surface of the support for receiving one or more protrusions on the first shell part.

Preferably, the one or more cavities comprise one or more pockets.

As such, the first shell part may comprise one or more protrusions for insertion into one or more cavities within or on the support.

Preferably, the support comprises one or more cavities for receiving one or more first protrusions on the first shell part, and one or more recesses for receiving one or more second protrusions on the first shell part.

Preferably, the one or more first protrusions project in a direction substantially perpendicular to the plane of the support. Preferably, the first shell part is a lower shell part and the one or more first protrusions project in an upward direction. Preferably, the one or more first protrusions are upwardly projecting protrusions.

Preferably, the one or more second protrusions project in a direction substantially parallel to the plane of the support. Preferably, the first shell part is a lower shell part and the one or more second protrusions project in a lateral/sideways direction. Preferably, the one or more second protrusions are lateral/sideways projecting protrusions.

Preferably, the one or more first protrusions are sized such that they engage with the one or more cavities before the one or more second protrusions engage with the one or more recesses when the support is moved into engagement with the first shell part.

Preferably, the one or more second protrusions are sized such that they disengage from the one or more recesses before the one or more first protrusions disengage from the one or more cavities when the support is moved out of engagement with the first shell part.

This provides rigidity to the first shell part both during and after engagement of a "snap-fit" connection, ensuring that the integrity of the connection is maintained at all times when the support and the first shell part are engaged.

Preferably, the first shell part is a lower shell part and the vertical distance between (i) the opening of the one or more cavities in the support, and (ii) the lower edge of the opening of the one or more recesses in the support, is less than the length of the one or more first protrusions on the first shell part.

In preferred embodiments:—

(a) the length of the one or more first protrusions is between about 2 mm and about 5 mm, preferably between about 2 mm and about 4 mm, preferably about 3 mm; and (b) the vertical distance between (i) the opening of the one or more cavities, and (ii) the lower edge of the opening of the one or more recesses is between about 0.5 mm and about 2 mm, preferably between about 0.5 mm and about 1.5 mm, preferably about 1 mm.

Preferably, the difference between:—

(a) the distance between (i) the opening of the one or more cavities, and (ii) the lower edge of the opening of the one or more recesses, and (b) the length of the one or more first protrusions, is between about 1 mm and about 4 mm, preferably between about 1 mm and about 3 mm, preferably about 2 mm.

Preferably, the one or more recesses are provided in the side of the support and the one or more cavities are provided on the underside of the support.

Preferably, the one or more male mating parts, preferably protrusions, protrude from a support facing surface of the first shell part.

Preferably, the one or more female mating parts, preferably recesses, are positioned at or near the edge of the support.

In addition to embodiments in which (a) the one or more recesses/cavities are provided in the first shell part and the one or more first and second protrusions are provided on the support or (b) wherein the one or more recesses/cavities are provided in the support and the one or more first and second protrusions are provided in the first shell part, it will be appreciated that further embodiments may provide that (c) the one or more recesses and one or more first protrusions are provided on or in the support and the one or more cavities and one or more second protrusions are provided on or in the first shell part, or (d) the one or more recesses and one or more first protrusions are provided on or in the first shell part and the one or more cavities and one or more second protrusions are provided on or in the support.

As such, in some embodiments it is preferred that the first shell part is a lower shell part and the vertical distance between (i) the opening of the one or more cavities in the first shell part, and (ii) the lower edge of the opening of the one or more recesses in the support, is less than the length of the one or more first protrusions on the support.

In such embodiments, it is preferred that:—

(a) the length of the one or more first protrusions is between about 2 mm and about 5 mm, preferably between about 2 mm and about 4 mm, preferably about 3 mm; and (b) the vertical distance between (i) the opening of the one or more cavities, and (ii) the lower edge of the opening of the one or more recesses is between about 0.5 mm and about 2 mm, preferably between about 0.5 mm and about 1.5 mm, preferably about 1 mm.

Preferably, the difference between:—

(a) the distance between (i) the opening of the one or more cavities, and (ii) the lower edge of the opening of the one or more recesses, and (b) the length of the one or more first protrusions, is between about 1 mm and about 4 mm, preferably between about 1 mm and about 3 mm, preferably about 2 mm.

In other embodiments it is preferred that the first shell part is a lower shell part and the vertical distance between (i) the opening of the one or more cavities in the support, and (ii) the upper edge of the opening of the one or more recesses in the first shell part, is less than the length of the one or more first protrusions on the first shell part.

In such embodiments, it is preferred that:—

(a) the length of the one or more first protrusions is between about 2 mm and about 5 mm, preferably between about 2 mm and about 4 mm, preferably about 3 mm; and (b) the vertical distance between (i) the opening of the one or more cavities, and (ii) the upper edge of the opening of the one or more recesses is between about 0.5 mm and about 2 mm, preferably between about 0.5 mm and about 1.5 mm, preferably about 1 mm.

Preferably, the difference between:—

(a) the distance between (i) the opening of the one or more cavities, and (ii) the upper edge of the opening of the one or more recesses, and (b) the length of the one or more first protrusions, is between about 1 mm and about 4 mm, preferably between about 1 mm and about 3 mm, preferably about 2 mm.

Preferably, in embodiments in which the one or more recesses are on the first shell part, the first shell part is a lower shell part and the vertical distance between (i) the opening of the one or more cavities, and (ii) the upper edge of the opening of the one or more recesses, is less than the length of the one or more first mating parts.

In such embodiments, it is preferred that:—

(a) the length of the one or more first mating parts is between about 2 mm and about 5 mm, preferably between about 2 mm and about 4 mm, preferably about 3 mm; and (b) the vertical distance between (i) the opening of the one or more cavities, and (ii) the upper edge of the opening of the one or more recesses is between about 0.5 mm and about 2 mm, preferably between about 0.5 mm and about 1.5 mm, preferably about 1 mm.

Preferably, the difference between:—

(a) the distance between (i) the opening of the one or more cavities, and (ii) the upper edge of the opening of the one or more recesses, and (b) the length of the one or more first mating parts, is between about 1 mm and about 4 mm, preferably between about 1 mm and about 3 mm, preferably about 2 mm.

Preferably, in embodiments in which the one or more recesses are on the support, the first shell part is a lower shell part and the vertical distance between (i) the opening of the one or more cavities, and (ii) the lower edge of the opening of the one or more recesses, is less than the length of the one or more first mating parts.

In such embodiments, it is preferred that:—

(a) the length of the one or more first mating parts is between about 2 mm and about 5 mm, preferably between about 2 mm and about 4 mm, preferably about 3 mm; and (b) the vertical distance between (i) the opening of the one or more cavities, and (ii) the lower edge of the opening of the one or more recesses is between about 0.5 mm and about 2 mm, preferably between about 0.5 mm and about 1.5 mm, preferably about 1 mm.

Preferably, the difference between:—

(a) the distance between (i) the opening of the one or more cavities, and (ii) the lower edge of the opening of the one or more recesses, and (b) the length of the one or more first mating parts, is between about 1 mm and about 4 mm, preferably between about 1 mm and about 3 mm, preferably about 2 mm.

Preferably, the outer surface of the one or more first mating parts, preferably the one or more protrusions, preferably the one or more first protrusions, is substantially flat.

Preferably, the inner surface of the one or more first mating parts, preferably the one or more protrusions, preferably the one or more first protrusions, is substantially flat.

Preferably, the one or more first mating parts, preferably the one or more protrusions, preferably the one or more first protrusions, comprise a tapered end.

Preferably, the inner surface of the one or more first mating parts, preferably the one or more protrusions, preferably the one or more first protrusions, is tapered.

Preferably, the inner surface of the one or more first mating parts, preferably the one or more protrusions, preferably the one or more first protrusions, is substantially flat between the tapered end and the support from which they protrude.

Preferably, the first shell part is a lower shell part, the inhaler comprises said third and fourth mating parts and the vertical distance between second and fourth mating parts is less than the length of the substantially flat part of the one or more first mating parts between the tapered end and the support.

Preferably, in embodiments in which the one or more recesses are on the first shell part, the first shell part is a lower shell part and the vertical distance between (i) the opening of the one or more cavities, and (ii) the upper edge of the opening of the one or more recesses, is less than the length of the substantially flat part of the one or more first mating parts between the tapered end and the support.

In such embodiments, it is preferred that:—

(a) the length of the substantially flat part is between about 1 mm and about 3 mm, preferably between about 1 mm and about 2 mm, preferably about 1.5 mm; and (b) the vertical distance between (i) the opening of the one or more cavities, and (ii) the upper edge of the opening of the one or more recesses is between about 0.5 mm and about 2 mm, preferably between about 0.5 mm and about 1.5 mm, preferably about 1 mm.

Preferably, the difference between:—

(a) the distance between (i) the opening of the one or more cavities, and (ii) the upper edge of the opening of the one or more recesses, and (b) the length of the substantially flat part, is between about 0.5 mm and about 2 mm, preferably between about 0.5 mm and about 1 mm, preferably about 0.5 mm.

Preferably, in embodiments in which the one or more recesses are on the support, the first shell part is a lower shell part and the vertical distance between (i) the opening of the one or more cavities, and (ii) the lower edge of the opening of the one or more recesses, is less than the length of the substantially flat part of the one or more first mating parts between the tapered end and the support.

In such embodiments, it is preferred that:—

(a) the length of the substantially flat part is between about 1 mm and about 3 mm, preferably between about 1 mm and about 2 mm, preferably about 1.5 mm; and (b) the vertical distance between (i) the opening of the one or more cavities, and (ii) the lower edge of the opening of the one or more recesses is between about 0.5 mm and about 2 mm, preferably between about 0.5 mm and about 1.5 mm, preferably about 1 mm.

Preferably, the difference between:—

(a) the distance between (i) the opening of the one or more cavities, and (ii) the lower edge of the opening of the one or more recesses, and (b) the length of the substantially flat part, is between about 0.5 mm and about 2 mm, preferably between about 0.5 mm and about 1 mm, preferably about 0.5 mm.

Preferably, the one or more first mating parts, preferably the one or more protrusions, are of substantially uniform thickness between the tapered end and the support from which they protrude.

Preferably, the trigger is shaped to at least partially fill the cut-out in the rim. This not only provides additional structural support to the first shell part, but also provides a convenient lever for allowing a user to lift the button, and the support, out of the first shell part.

Preferably, the trigger is shaped to bridge the gap in the rim formed by the cut-out.

Preferably, the trigger comprises a protrusion for at least partially filling the cut-out in the rim. Preferably, the protrusion is shaped to bridge the gap in the rim formed by the cut-out.

Preferably, the support is shaped to at least partially fill the cut-out in the rim. In a similar manner to the shape of the trigger, this not only provides additional structural support to the first (lower) shell part, but also provides a convenient lever for allowing a user to lift the support out of the first (lower) shell part.

Preferably, the support is shaped to bridge the gap in the rim formed by the cut-out.

Preferably, the support comprises a protrusion for at least partially filling the cut-out in the rim. Preferably, the protrusion is shaped to bridge the gap in the rim formed by the cut-out.

Preferably, the cut-out in the rim is at least partially filled by both the trigger and the support.

Preferably, both the trigger and the support bridge the gap in the rim formed by the cut-out.

Preferably, the rim of the second shell part is shaped to overlap the cut-out in the rim of the first shell part. This provides additional structural support and protection to the inhaler around the cut-out when the outer shell is in a closed position.

Preferably, the first and second shell parts are hinged together with the hinge positioned on the outside of the first shell part below the rim of the first shell part.

Further preferably, the rim of the second shell part is shaped to overlap the first shell part adjacent said hinge. This is particularly advantageous because it provides additional structural support to the hinge when the outer shell is in a closed position.

Preferably, the rim of the second shell part overlaps the first shell part adjacent the hinge and over the cut-out by a greater amount than at a position between the hinge and the cut-out. This is advantageous because such a shaped rim profile has been found to not only increase the strength of the second shell part, but also to minimise the amount of material used in the outer shell.

Preferably, the first shell part comprises one or more ribs for providing structural support to the first shell part.

Preferably, the trigger is supported by the support.

Preferably, the trigger is held in slideable engagement with the support.

Preferably, the trigger is moveable along one or more channels of the support.

Preferably, the trigger is moveable along a pair of channels.

Preferably, the trigger comprises one or more protrusions for slideable engagement with the support, preferably with one or more channels of the support.

Preferably, the trigger comprises a first protrusion for slideable engagement with a first channel of the support and a second protrusion for slideable engagement with a second channel of the support.

Preferably, the one or more channels are provided on the underside of the support.

Preferably, the cut-out is narrower than the aperture, said trigger comprising a main body and a projection, wherein the cut-out is shaped to accommodate said projection and the aperture is shaped to accommodate the main body.

According to another aspect of the present invention, there is provided an inhaler for inhalation of an inhalable dry powder, the inhaler comprising:—

(a) an outer shell comprising a first shell part and a second shell part;

(b) a capsule holder comprising a chamber for holding a capsule, a capsule breaker for breaking open a capsule held within the chamber and a trigger for causing the capsule breaker to break open a capsule;

(c) a support for supporting the capsule holder; and (d) an outlet for passage of dry powder from the capsule into a user, wherein the capsule holder is positioned in the first shell part, wherein the first shell part comprises an aperture through which the trigger protrudes, wherein the aperture comprises a cut-out in the rim of the first shell part and through which the trigger may pass when the capsule holder is removed from the first shell part, and wherein at least a part of the wall of the first shell part comprises a thickened wall.

Preferably, the thickened wall comprises a double-skinned wall.

Preferably, the first shell part comprises one or more cavities within the thickened wall of the first shell part for receiving one or more protrusions on the support.

Preferably, the one or more cavities comprise one or more pockets.

Preferably, the thickened wall at least partially surrounds the cut-out and/or the aperture.

Preferably, the thickened wall is provided at or near each side of the cut out.

Preferably, the thickened wall is provided along at least a part of each side of the aperture adjacent the cut-out. Put another way, it is preferred that the thickened wall is provided each side of an upper part of the aperture.

Preferably, at least a part of the thickened wall of the first shell part is a double-skinned wall comprising an inner skin and outer skin.

Preferably, at least a part of the thickened wall of the first shell part is a double-skinned wall comprising an inner skin and outer skin, with one or more cavities formed between said inner and outer skins.

Preferably, the double-skinned wall comprises one or more cross members for dividing the space between said inner and outer skins into multiple cavities.

Preferably, the thickness of the thickened wall, preferably the double-skinned wall, tapers from a greater thickness at a point away from the cut-out to a lesser thickness at or near the cut-out.

Preferably, the length of the thickened wall, preferably the double-skinned wall, tapers from a greater length at or near the rim of the first shell part to a lesser length at a point away from the rim of the first shell part, for example at or near the base of the first shell part.

According to a further aspect of the present invention, there is provided an inhaler for inhalation of an inhalable dry powder, the inhaler comprising:—

(a) an outer shell comprising a first shell part and a second shell part;

(b) a capsule holder comprising a chamber for holding a capsule, a capsule breaker for breaking open a capsule held within the chamber and a trigger for causing the capsule breaker to break open a capsule;

(c) a support for supporting the capsule holder; and (d) an outlet for passage of dry powder from the capsule into a user, wherein the capsule holder is positioned in the first shell part, wherein the first shell part comprises an aperture through which the trigger protrudes, wherein the aperture comprises a cut-out in the rim of the first shell part through which the trigger may pass when the capsule holder is removed from the first shell part, wherein said cut-out is narrower than the aperture, said trigger comprising a main body and a projection, wherein the cut-out is shaped to accommodate said projection and the aperture is shaped to accommodate the main body.

Such an arrangement is particularly effective at providing strength to the outer wall of the inhaler because the trigger can still be easily removed from the first shell part but at the same time, the size of the cut-out, and thus the impact on the stability of the first shell part, is reduced.

It will be appreciated that reference to the cut-out being narrower than the aperture is with reference to the respective widths of the cut-out and aperture when the inhaler is viewed from the front. This is shown with particular reference to FIG. 5.

According to another aspect of the present invention, there is provided an inhaler for inhalation of an inhalable dry powder, the inhaler comprising:—

(a) an outer shell comprising a first shell part and a second shell part;

(b) a capsule holder comprising a chamber for holding a capsule, a capsule breaker for breaking open a capsule held within the chamber and a trigger for causing the capsule breaker to break open a capsule;

(c) a support for supporting the capsule holder; and (d) an outlet for passage of dry powder from the capsule into a user, wherein the capsule holder is positioned in the first shell part, wherein the first shell part comprises an aperture through which the trigger protrudes; and wherein the trigger is supported by the support.

Preferably, the aperture comprises a cut-out in the rim of the first shell part through which the trigger may pass when the capsule holder is removed from the first shell part.

Preferably, the trigger is held in slideable engagement with the support.

Preferably, the trigger is moveable along one or more channels of the support.

Preferably, the trigger is moveable along a pair of channels.

Preferably, the trigger comprises one or more protrusions for slideable engagement with the support, preferably with one or more channels of the support.

Preferably, the trigger comprises a first protrusion for slideable engagement with a first channel of the support and a second protrusion for slideable engagement with a second channel of the support.

Preferably, the one or more channels are provided on the underside of the support.

According to a further aspect of the present invention, there is provided an inhaler for inhalation of an inhalable dry powder, the inhaler comprising:—

(a) an outer shell comprising a first shell part and a second shell part;

(b) a capsule holder comprising a chamber for holding a capsule, a capsule breaker for breaking open a capsule held within the chamber and a trigger for causing the capsule breaker to break open a capsule;

(c) a support for supporting the capsule holder; and (d) an outlet for passage of dry powder from the capsule into a user, wherein the capsule holder is positioned in the first shell part, wherein the first shell part comprises an aperture through which the trigger protrudes, wherein the aperture comprises a cut-out in the rim of the first shell part and through which the trigger may pass when the capsule holder is removed from the first shell part, and wherein the support comprises one or more first mating parts for mating with one or more second mating parts on the first shell part and one or more third mating parts for mating with one or more fourth mating parts on the first shell part.

Preferably, engagement of the one or more third mating parts with the one or more fourth mating parts forms a connection, preferably a snap-fit connection, between the support and the first shell part.

Preferably, the connection formed between the support and the first shell part is maintained by engagement of the one or more first mating parts with the one or more second mating parts.

It will be appreciated that reference to "one or more" includes reference to "a plurality".

It will be appreciated that reference to "at least partially" includes reference to "completely".

It will be appreciated that reference to "at least a part of" includes reference to "all".

Within this specification, the term "about" means plus or minus 20%, more preferably plus or minus 10%, even more preferably plus or minus 5%, most preferably plus or minus 2%.

Preferably, reference to "vertical" is with reference to a direction substantially perpendicular to the plane of the support.

In embodiments wherein the first mating parts are male mating parts, it will be appreciated that "length of the one or more first mating parts" means the distance the one or more first mating parts, preferably one or more protrusions, protrude from the support.

In embodiments wherein the second mating parts are male mating parts, it will be appreciated that "length of the one or more second mating parts" means the distance the one or more second mating parts, preferably protrusions, protrude from the first shell part.

Within this specification, it will be appreciated that reference to "depth", for example in relation to a recess or a cavity, should be given its usual meaning in relation to the depth of a recess or cavity, for example the distance the recess or cavity protrudes into the support or the first shell part.

Within this specification, it will be appreciated that "substantially perpendicular to the plane of the support" means between about 80 degrees and about 100 degrees to the plane of the support, preferably between about 85 degrees and about 95 degrees, preferably between about 90 degrees, preferably 90 degrees to the plane of the support.

Within this specification, it will be appreciated that "substantially parallel to the plane of the support" means between with about 10 degrees to the plane of the support, preferably within about 5 degrees, preferably within about 3 degrees to the plane of the support, preferably parallel to the plane of the support.

Preferably "substantially flat" means flat.

Preferably, "substantially flat" means not tapered.

It will be appreciated that reference to "walls of the first shell part" includes reference to opposing walls of the shell part. For example, the first shell part has opposing walls on opposite sides of the opening bordered by the rim.

In another aspect of the present invention, there is provided an inhaler for inhalation of an inhalable dry powder, the inhaler comprising:—

(a) an outer shell comprising a first shell part and a second shell part;

(b) a capsule holder comprising a chamber for holding a capsule, a capsule breaker for breaking open a capsule held within the chamber and a trigger for causing the capsule breaker to break open a capsule;

(c) a support for supporting the capsule holder; and (d) an outlet for passage of dry powder from the capsule into a user, wherein the capsule holder is positioned in the first shell part, wherein the first shell part comprises an aperture through which the trigger protrudes, wherein the aperture comprises a cut-out in the rim of the first shell part and through which the trigger may pass when the capsule holder is removed from the first shell part, and wherein the support comprises one or more first mating parts for mating with one or more second mating parts on the first shell part, said first and second mating parts preventing outward movement of the/a wall of the first shell part when said first and second mating parts are mutually engaged.

Within this specification, it is preferred that reference to "preventing outward movement" means that the/a wall or walls cannot move outwards by more than about 1 mm, preferably by more than about 0.8 mm, preferably by more than about 0.5 mm, preferably by more than about 0.3 mm, preferably by more than about 0.2 mm, preferably by more than about 0.1 mm.

In embodiments comprising one or more third and fourth mating parts, it is preferred that "preventing outward movement" means that the/a wall or walls cannot move outwards more than the length or depth of the one or more third mating parts.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the present invention described herein and vice versa, as appropriate.

DETAILED DESCRIPTION

Example embodiments of the present invention will now be described with reference to the accompanying Figures, in which:—

Figure 1:
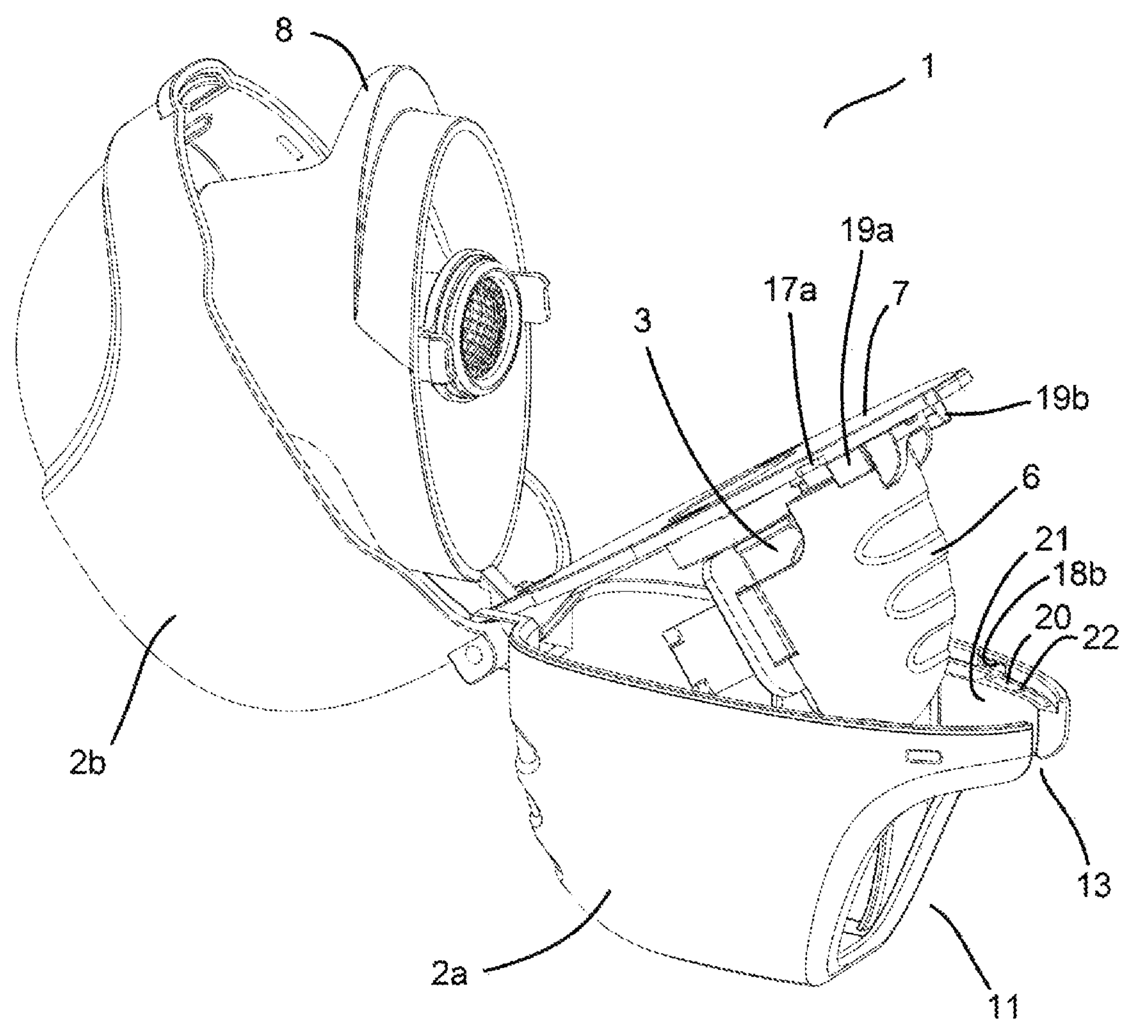
FIG. 1 shows a view of the inhaler of the present invention in which the outer shell is hinged open, the hinged plate and mouthpiece are in an open configuration and in which the trigger has been pressed inwards.

The present invention relates to inhalers for the inhalation of dry powders from capsules in which the structural integrity of the outer casing is improved.

With reference to the Figures, an inhaler 1 of the present invention includes an outer shell 2 comprising a first shell part 2*a* and a second shell part 2*b*, a capsule holder 3 comprising a chamber 4 for holding a capsule (not shown), a capsule breaker 5 for breaking open a capsule held within the chamber 4 and a trigger 6, in the form of a button 6, for causing the capsule breaker 5 to break open a capsule. In the example shown, the capsule breaker 5 comprises a pair of pointed rods 5*a*, 5*b*.

Figure 3:
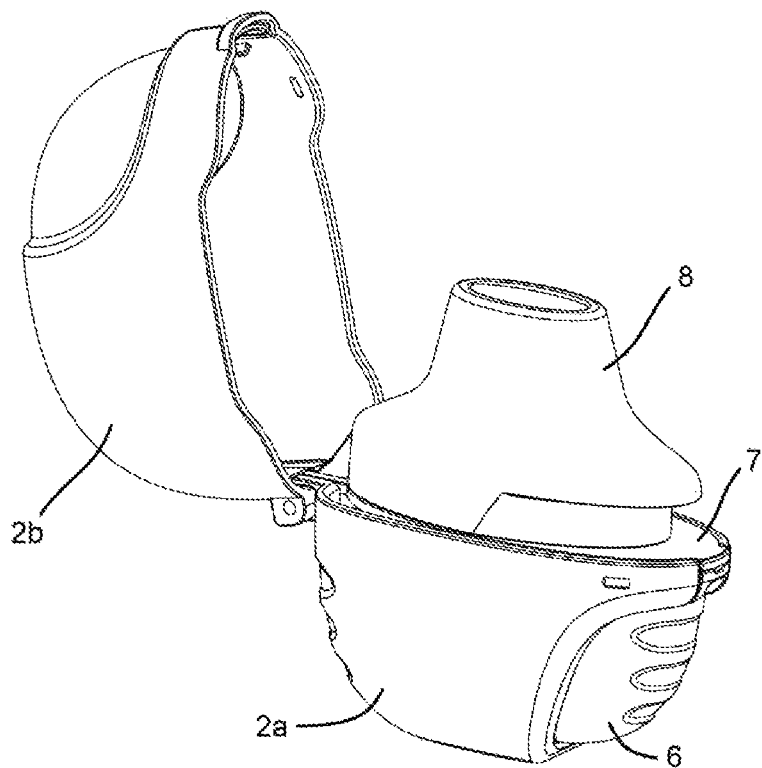
FIG. 3 shows a view of the inhaler of the present invention in which the outer shell is hinged open and the hinged plate and mouthpiece are in a closed configuration.
Figure 4:
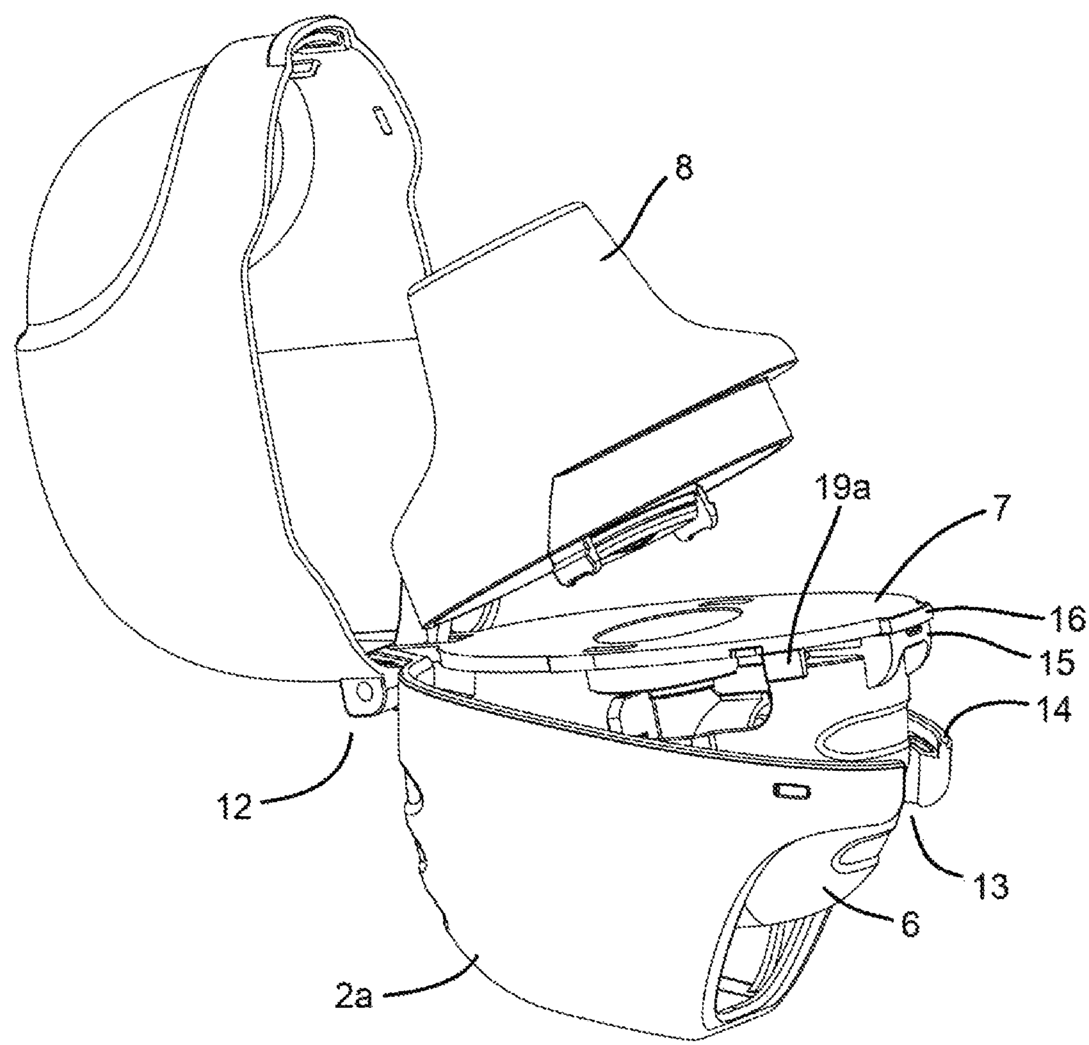
FIG. 4 shows a view of the inhaler of the present invention in which the outer shell is hinged open, the hinged plate and mouthpiece are in an open configuration and in which the trigger is at an "at rest" position.

The capsule holder 3 is held in position by a support 7 which, in the example shown, is a hinged plate 7. With particular reference to FIGS. 3 and 4, during normal use, the hinged plate 7 is releasably connected to the first shell part 2*a*, such that the capsule holder 3 is positioned within the first shell part 2*a*.

The inhaler also includes an outlet 8, in the form of a mouthpiece 8, through which a user can inhale powder from a broken capsule held within the chamber 4.

Figure 6:
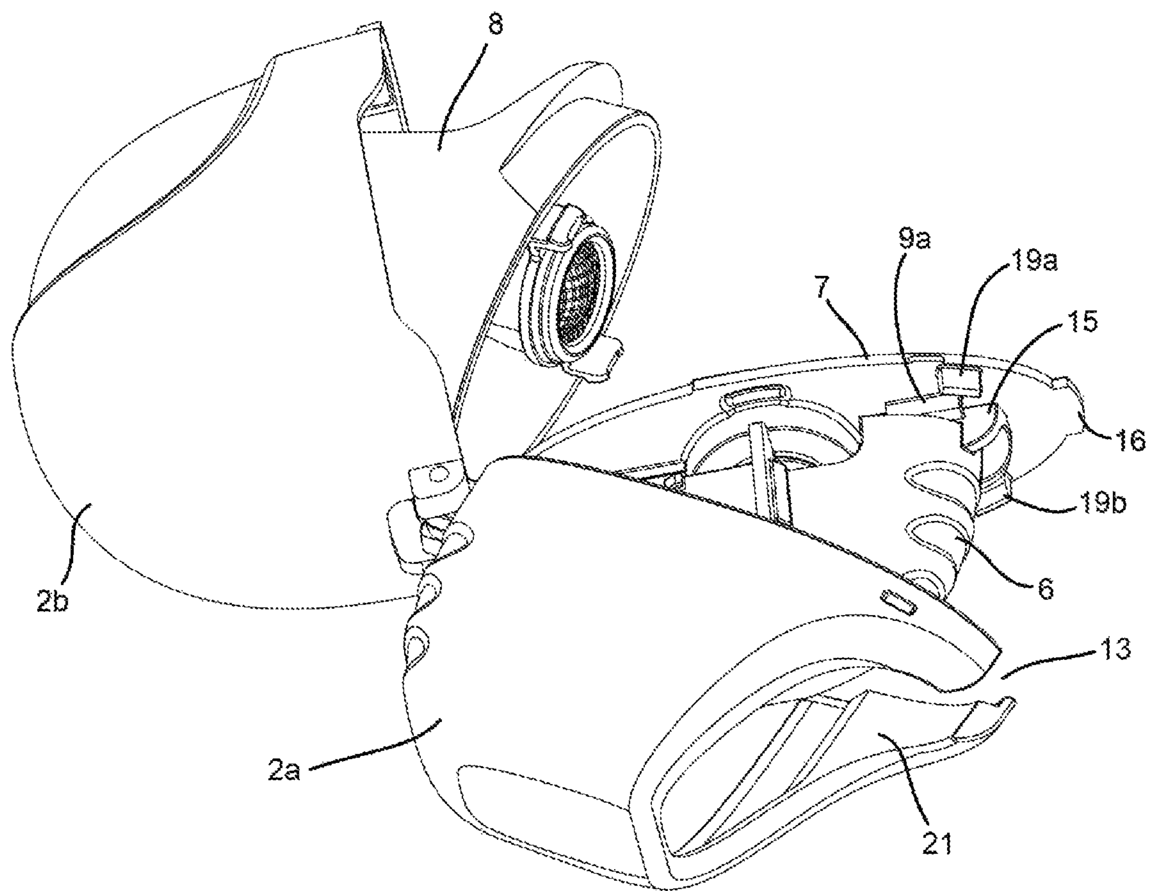
FIG. 6 shows a perspective view of the inhaler as shown in FIG. 1 from below.

As shown in FIG. 6, the hinged plate 7 also supports the trigger 6 with the trigger 6 in slideable engagement with the underside of the hinged plate 7 via a pair of channels 9*a*, 9*b* along which lateral flanges 10*a*, 10*b* of the trigger 6 slide. This is particularly advantageous because it ensures correct alignment of the rods 5*a*, 5*b* when the trigger 6 is pressed, even if the trigger 6 flexes to some extent during operation.

Figure 7:
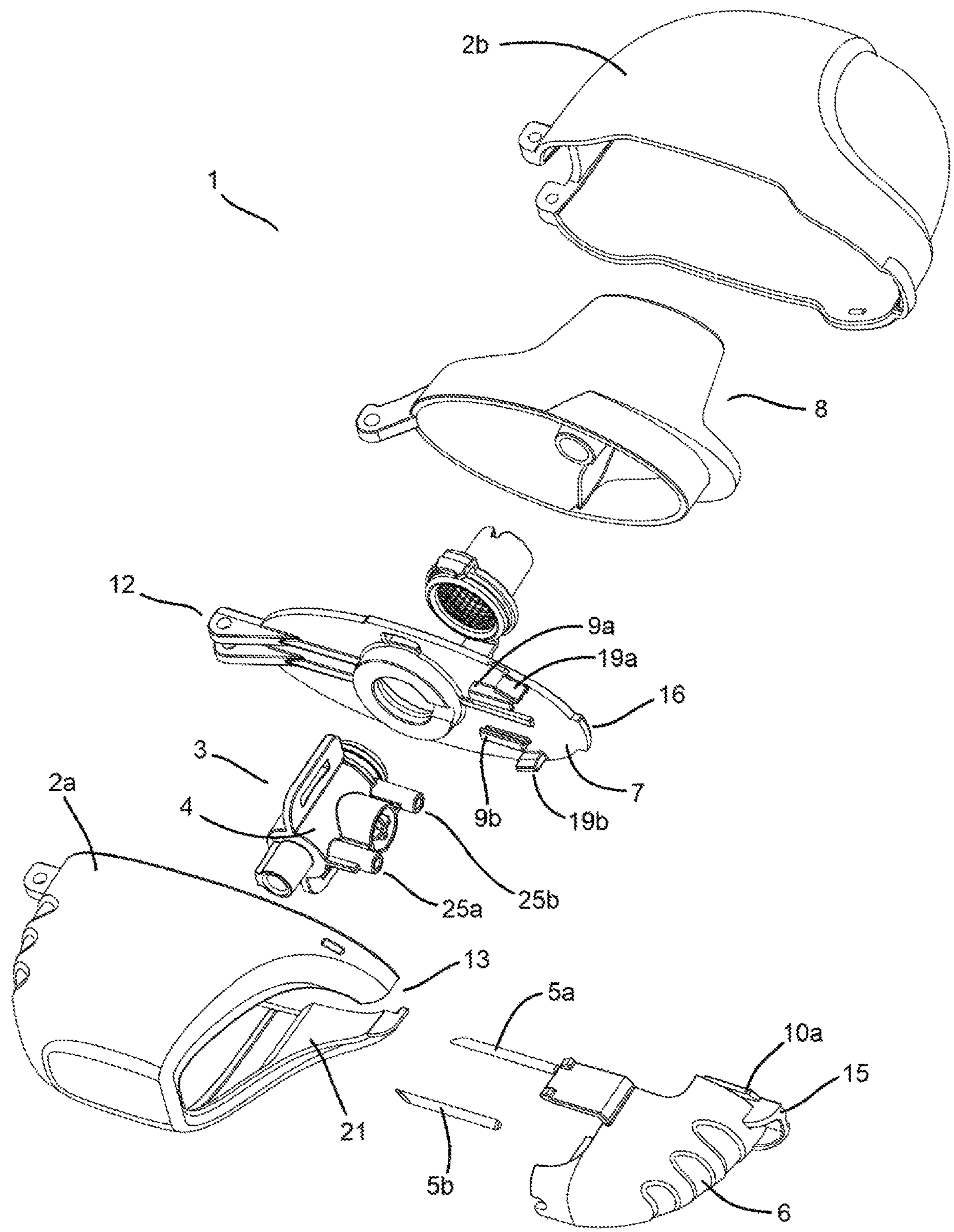
FIG. 7 shows an exploded view of the inhaler of the present invention.
Figure 8:
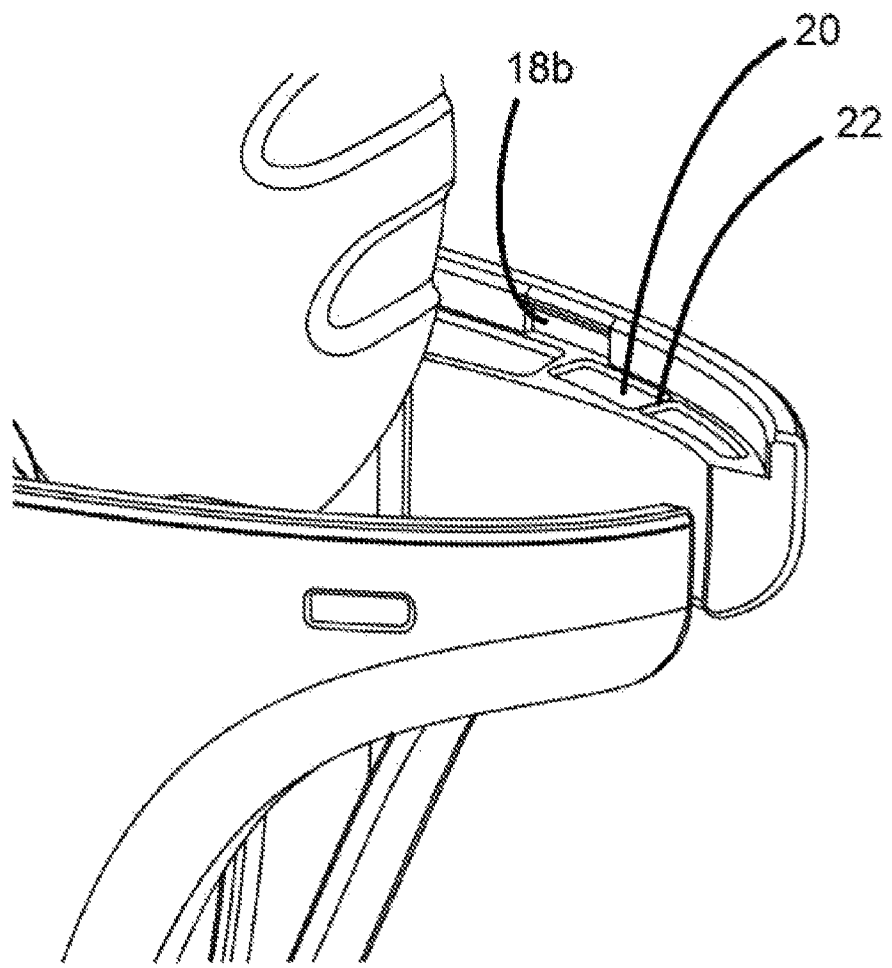
FIG. 8 shows an enlarged view of the double-skinned wall of the inhaler.

As shown in FIGS. 3 and 7, when the hinged plate 7 is connected to the first shell part 2*a*, i.e. during normal use, the trigger 6 protrudes through an aperture 11 in the wall of the first shell part 2*a*. When at rest, the trigger 6 is urged by one or more springs (not shown) towards a position in which it protrudes through the aperture 11 and at which the pointed rods 5*a*, 5*b* are not pushed into contact with a capsule held within the chamber 4. The trigger 6 is shown in an at rest position in FIGS. 2, 3, 4 and 5.

When a user wishes to break a capsule held within the chamber 4 of the capsule holder 3, the trigger 6 is pushed inwards towards the capsule holder 3. This causes the pointed rods 5*a*, 5*b* to break open the capsule and release powder contained within the capsule into the chamber 4. The trigger 6 is shown in a "pushed in" position in FIGS. 1 and 6.

As will be appreciated, with the trigger 6 engaged with the channels 9*a*, 9*b*, when the hinged plate 7 is released from the first shell part 2*a* to allow the hinged plate 7 to pivot about its hinge 12, the trigger 6 will also be removed from the first shell part 2*a*. This is further assisted by the location of the rods 5*a*, 5*b* within receiving channels 25*a*, 25*b* of the capsule holder 3. Conveniently, this is facilitated by a cut-out 13 in the rim 14 of the first shell part 2*a* through which the trigger 6 passes as the hinged plate 7 is pivoted away from the first shell part 2*a*.

Unfortunately, whilst the provision of the cut-out 13 greatly improves usability of the inhaler, this can reduce the rigidity of the first shell part 2*a* and thus affect reliability of the connection made between the hinged plate 7 and the first shell part 2*a*. As will be appreciated, it is important for the hinged plate 7 to remain connected to the first shell part 2*a* during normal use so that the position of the capsule holder relative to the trigger 6 is maintained and so that the capsule holder 3 and trigger 6 are not released from the first shell part 2*a* when the mouthpiece 8 is opened, i.e. when the mouthpiece 8 is pivoted upwards and away from the hinged plate 7, or when the trigger 6 is pressed. If the first shell part 2*a* is not sufficiently rigid, the "snap-fit" connection between the hinged plate 7 and the first shell part 2*a* can release unexpectedly, which is clearly undesirable.

Figure 5:
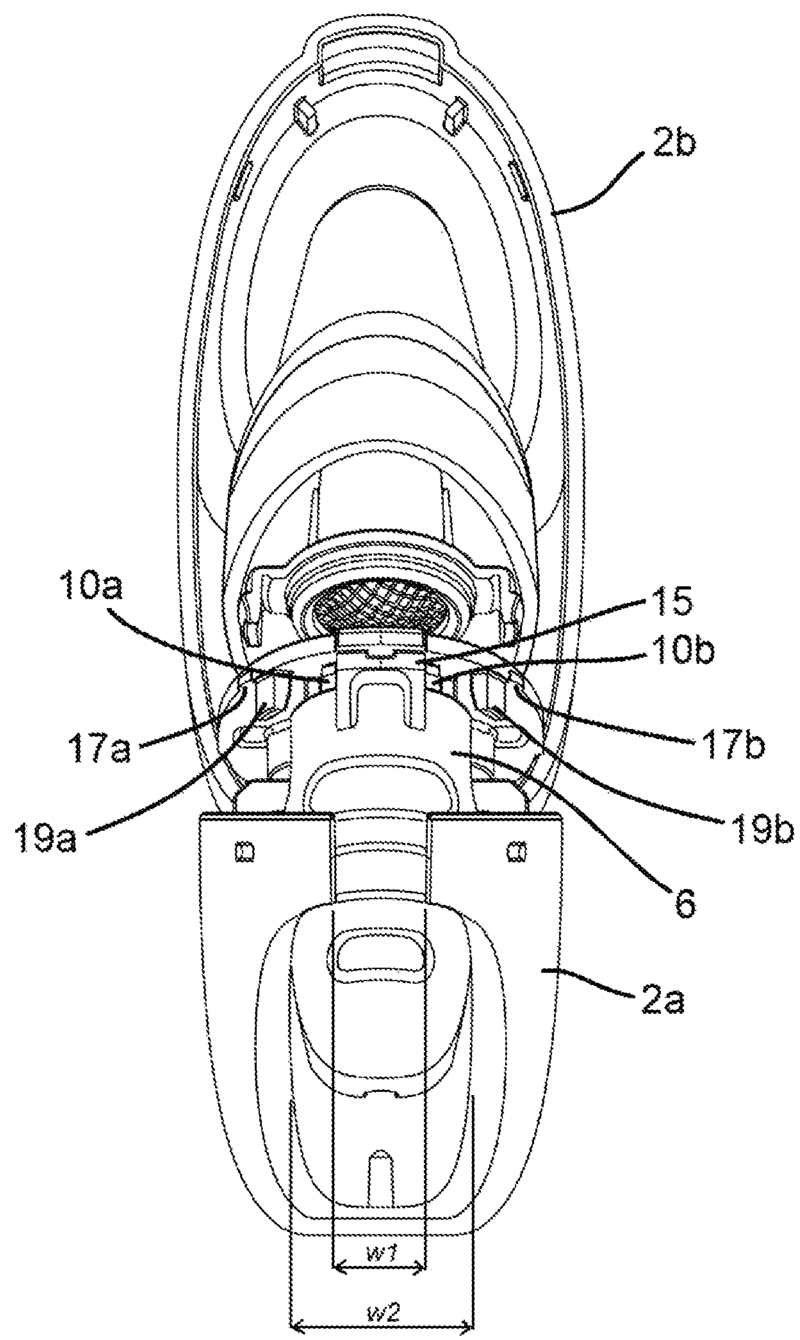
FIG. 5 shows a front view of inhaler as shown in FIG. 4.

As also shown in FIG. 3, and with additional reference to the shape of the trigger 6 shown in FIGS. 4, 5 and 7, the trigger 6 includes a projection 15, which sits within the cut-out of the rim in an "at rest" position of the trigger 6. This adds structural support to the first shell part 2*a* preventing inward movement of the first shell part 2*a* around the cut-out 13. In order to provide additional support, the hinged plate 7 also includes a projection 16 which sits within the cut-out 13 of the rim 14.

With particular reference to FIG. 5, the cut-out 13 is narrower than the aperture 11, the cut-out 13 is shaped to accommodate the projection 15 and the aperture 11 is shaped to accommodate the main body 26 of the trigger 6. In this respect, the width w1 of the cut-out 13 is less than the width w2 of the aperture 11.

Whilst the projections 15, 16 prevent inward movement of the walls of the first shell part 2*a*, they do not prevent outward movement. In fact, such outward movement is of greater risk to the snap-fit connection of the hinged plate 7 to the first shell part 2*a*, because the connection relies on protrusions 17*a*, 17*b* on the hinged plate 7 engaging with a "clip-fit" to the recesses 18*a*, 18*b* on the internal wall of the first shell part 2*a*. Accordingly, if the walls of the first shell part 2*a* are permitted to move outward, the protrusions 17*a*, 17*b* will no longer sit securely within the recesses 18*a*, 18*b*.

Figure 9:
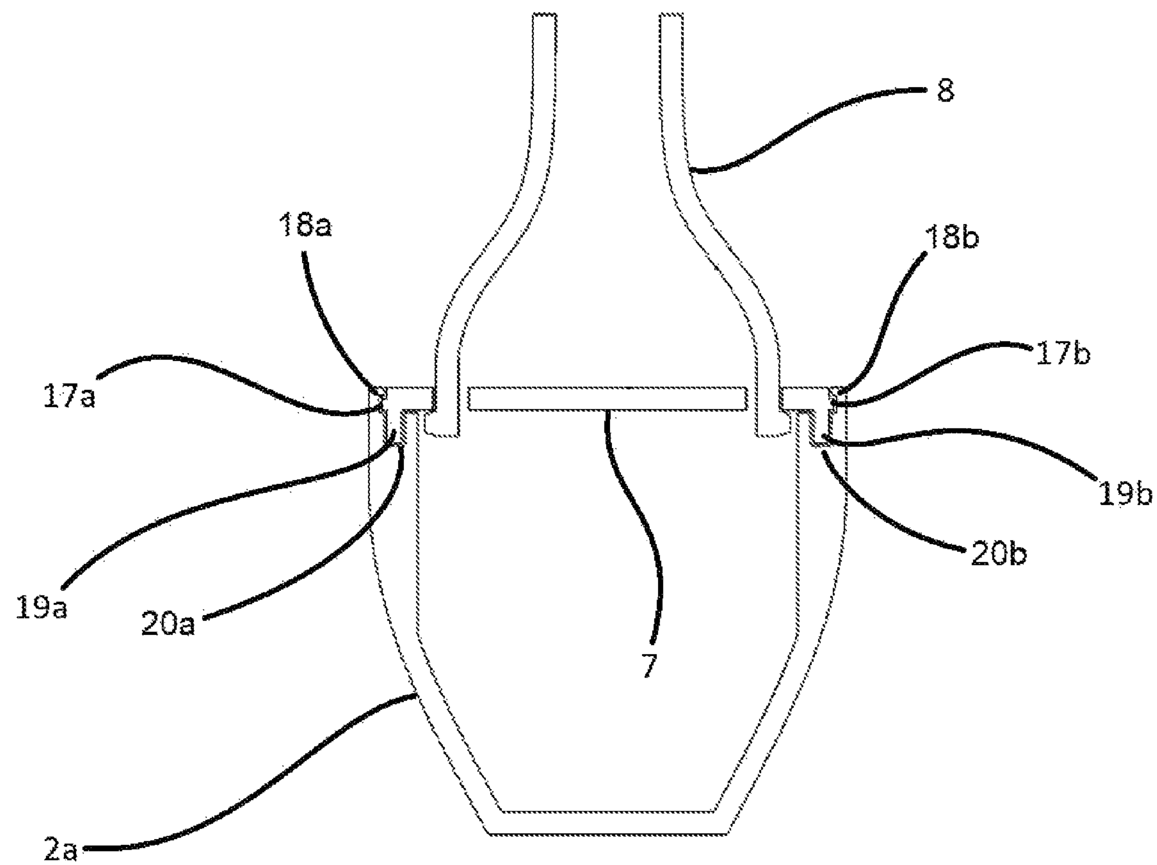
FIG. 9 is a schematic showing positions of the protrusions and recesses/cavities of the support and first shell part.
Figure 10:
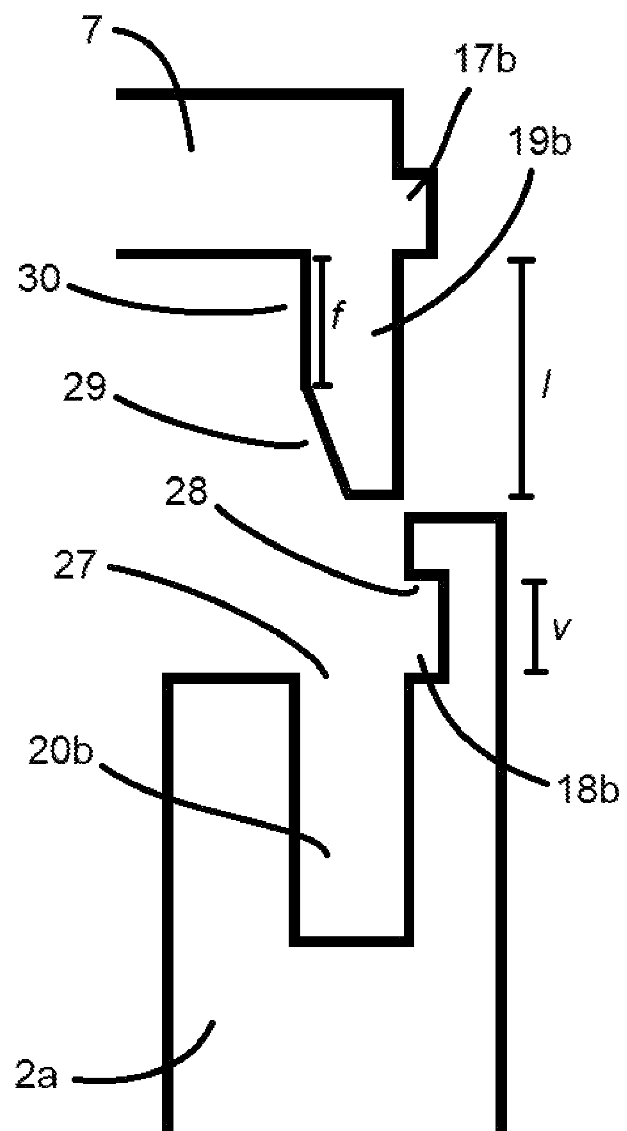
FIG. 10 shows an enlarged view of part of FIG. 9 showing the positions and relative sizes of the protrusions and recesses/cavities of the support and first shell part.

With particular reference to FIGS. 9 and 10, in order to prevent outward movement of the walls of the first shell part 2*a*, the hinged plate 7 includes a pair of downward projecting protrusions 19*a*, 19*b*, which are received within cavities 20*a*, 20*b* formed within a double-skinned wall 21 of the first shell part 2*a*. In the example shown, the length/of the protrusions is 3 mm. The protrusions 19*a*, 19*b* have tapered ends 29 to allow for misalignment during insertion into the cavities 20*a*, 20*b* and to pull the walls of the first shell part 2*a* in tight. The remainder of each protrusion 19*a*, 19*b* is substantially uniform in thickness to allow the protrusions 17*a*, 17*b* to "snap-fit" with the recesses 18*a*, 18*b* on the first shell part 2*a* as the hinged plate 7 is lowered. The inner surfaces 30 of the protrusions 19*a*, 19*b* between the tapered ends and the hinged plate 7 are flat. In the example shown, this flat part f of the protrusions is 1.5 mm in length. This means that the wall is prevented from moving outwards even if there is a small amount of rotational travel of the hinged plate 7. This also ensures that the hinged plate 7 disengages from the first shell part 2*a* with a controlled force.

The vertical distance v between the opening 27 of the cavities 20*a*, 20*b* and the upper edge 28 of the recesses 18*a*, 18*b* is 1 mm. As a result, there is a difference of 2 mm between said vertical distance and the length of the protrusions 19*a*, 19*b* or a difference of 0.5 mm between said vertical distance and the length of the flat part 30. This means that, when the hinged plate 7 is moved out of engagement with the first shell part, the protrusions 17*a*, 17*b* disengage from the recesses 18*a*, 18*b* before the protrusions 19*a*, 19*b* disengage from the cavities 20*a*, 20*b*.

This also means that when the hinged plate 7 is moved into engagement with the first shell part 2*a*, the protrusions 19*a*, 19*b* and cavities 20*a*, 20*b* engage before the protrusions 17*a*, 17*b* and recesses 18*a*, 18*b*. This allows engagement of the protrusions 19*a*, 19*b* and cavities 20*a*, 20*b* to stabilise the first shell part 2*a* and allow reliable "snap-fit" engagement of the protrusions 17*a*, 17*b* and recesses 18*a*, 18*b*.

FIG. 9 shows a schematic cross-sectional view of the first shell part 2*a* and hinged plate 7 showing the relative positions and sizes of protrusions 17*a*, 17*b*, 19*a*, 19*b*, recesses 18*a*, 18*b* and cavities 20*a*, 20*b*.

With the protrusions 19*a*, 19*b* positioned within the cavities 20*a*, 20*b*, outward movement of the first shell part walls is prevented. The length of the protrusions 19*a*, 19*b* is such that they engage with the cavities 20*a*, 20*b* before the protrusions 17*a*, 17*b* engage in their "snap-fit" connection with recesses 18*a*, 18*b* when the hinged plate 7 is moved into engagement with the first shell part 2*a*, and they disengage with the cavities 20*a*, 20*b* after the "snap-fit" connection disengages as the hinged plate 7 moves out of engagement with the first shell part 2*a*. This provides rigidity to the walls of the first shell part 2*a* both during and after engagement of the "snap-fit" connection, ensuring that the integrity of the "snap-fit" connection is maintained at all times when the hinged plate 7 and the first shell part 2*a* are engaged.

The double-skinned wall 21 of the first shell part 2*a* not only acts to prevent outward movement, but also provides additional structural rigidity to the first shell part 2*a*. In this respect, and with particular reference to FIG. 1, the double-skinned wall 21 provides a re-enforced outer wall on either side of the cut out and an upper part of the aperture 11.

As also shown in FIG. 1, the double-skinned wall 21 includes cross members 22, which divide the space between said inner and outer skins of the double-skinned wall 21 into multiple cavities 20. Further, the thickness of the double-skinned wall tapers from a greater thickness distal from the cut-out 13 to a lesser thickness at or near the cut-out 13. This arrangement of a tapered double-skinned wall with cross members forming multiple cavities has been found to be particularly effective at not only preventing outward movement of the walls of the first shell part 2*a* via engagement with the downward projections protrusions 19 of the hinged plate 7 but also preventing such outward movement via the structural support imparted by the arrangement.

The first shell part 2*a* is also provided with a plurality of ribs 24 for providing structural support to the first shell part 2*a*.

The first and second shell parts 2*a*, 2*b* are hinged together by a hinge 12 positioned on the outside of the first shell 2*a* part below the rim 14 of the first shell part 2*a*.

Figure 2:
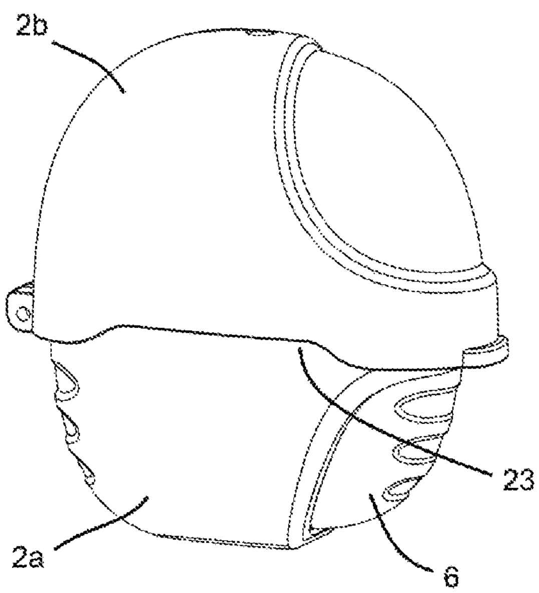
FIG. 2 shows a view of the inhaler of the present invention in which the outer shell is closed.

With particular reference to FIG. 2, the second shell part 2*b* is shaped so that its rim 23 overlaps the cut-out 13 in the rim 14 of the first shell part 2*a*. This provides additional structural support to the inhaler around the cut-out 13 when the outer shell is in a closed position. The rim 23 of the second shell part 2*b* is also shaped to overlap the first shell part 2*a* adjacent the hinge 12. This is also advantageous because it provides additional structural support to the hinge 12 when the outer shell 2*a*, 2*b* is in a closed position.

As will also be evident from FIG. 2, the rim 23 of the second shell part 2*b* overlaps the first shell part 2*a* adjacent the hinge 12 and over the cut-out 13 by a greater amount than at a position between the hinge 12 and the cut-out 13. This is advantageous because such a shaped rim profile has been found to not only increase the strength of the second shell part 2*b* but also to minimise the amount of material forming the outer shell 2*a*, 2*b*.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications are covered by the appended claims.

The invention claimed is:

1. An inhaler for inhalation of an inhalable dry powder, the inhaler comprising:

(a) an outer shell comprising a first shell part and a second shell part;

(b) a capsule holder comprising a chamber for holding a capsule, a capsule breaker for breaking open the capsule held within the chamber and a trigger for causing the capsule breaker to break open the capsule;

(c) a support for supporting the capsule holder; and (d) an outlet for passage of dry powder from the capsule into a user, wherein the capsule holder is positioned in the first shell part, wherein the first shell part comprises an aperture through which the trigger protrudes, wherein the first shell part comprises a rim and wherein the aperture comprises a cut-out in the rim of the first shell part and through which the trigger is able to pass when the capsule holder is removed from the first shell part, and wherein the support comprises one or more downwardly projecting protrusions on a first side of a bottom surface of the support and one or more downwardly projecting protrusions on a second side of the bottom surface of the support, the one or more downwardly projecting protrusions on the first side and the second side of the support is configured to mate with one or more cavities formed within a first side wall of the first shell part and one or more cavities formed within a second side wall of the first shell part, respectively, wherein the cut-out is formed between the first side wall and the second side wall, said protrusions of the first and second sides of the support and the one or more cavities of the first side wall and second side wall preventing outward movement of the first and second side walls of the first shell part when said protrusions of the first side and the second side of the support and the one or more cavities of the first and second side walls are mutually engaged.

2. An inhaler according to claim 1, wherein the one or more cavities of each of the first and second side walls are formed in a thickened part of the first side wall and the second side wall of the first shell part.

3. An inhaler according to claim 2, wherein the thickened part of the first and second side walls partially surrounds the cut-out and/or the aperture.

4. An inhaler according to claim 2, wherein at least a part of the thickened part of the first and second side walls comprises a double-skinned wall comprising an inner skin and outer skin, with said one or more cavities of each of first and second side walls formed between said inner and outer skins of each of the first side wall and second side wall.

5. An inhaler according to claim 4, wherein each of the one or more cavities of each of the first and second side walls comprise multiple cavities, and wherein the double-skinned wall of each of the first and second side walls comprises one or more cross members for dividing a space between said inner and outer skins of each of the first side wall and the second side wall into the multiple cavities.

6. An inhaler according to claim 2, wherein the thickness of the thickened part of each of the first and second side walls tapers from a greater thickness at a point away from the cut-out to a lesser thickness at or near the cut-out.

7. An inhaler according to claim 1, wherein the one or more downwardly projecting protrusions of the first side of the support protrude from a first shell part facing surface of the first side of the support and the one or more downwardly projecting protrusions of the second side of the support protrude from a first shell part facing surface of the second side of the support.

8. An inhaler according to claim 1, wherein the support comprises one or more first mating parts for mating with one or more second mating parts on the first shell part.

9. An inhaler according to claim 8, wherein the one or more first mating parts comprise one or more male mating parts, and the one or more second mating parts comprise one or more female mating parts.

10. An inhaler according to claim 8, wherein engagement of the one or more first mating parts with the one or more second mating parts forms a connection between the support and the first shell part and wherein the connection formed between the support and the first shell part is maintained by engagement of the one or more downwardly projecting protrusions of each of the first side and second side of the support with the one or more cavities of each of the first side wall and second side wall of the first shell.

11. An inhaler according to 10, wherein the one or more first mating parts extend in a direction substantially parallel to a plane of the support.

12. An inhaler according to claim 1, wherein the one or more downwardly projecting protrusions of each of the first and second sides of the support extend in a direction substantially perpendicular to a plane of the support.

13. An inhaler according to claim 1, wherein the cut-out is narrower than the aperture, said trigger comprising a main body and a projection, wherein the cut-out is shaped to accommodate said projection and the aperture is shaped to accommodate the main body.

* * * * *